United States Patent [19]

Kenny

[11] 4,262,982
[45] * Apr. 21, 1981

[54] ELECTRICAL SOCKET USEFUL FOR CONNECTING AN ELECTRODE CATHETER TO A CARDIAC PACEMAKER CASING

[75] Inventor: John Kenny, Prestwick, Scotland

[73] Assignee: Needle Industries Ltd., Studley, England

[*] Notice: The portion of the term of this patent subsequent to Sep. 2, 1997, has been disclaimed.

[21] Appl. No.: 29,280

[22] Filed: Apr. 11, 1979

Related U.S. Application Data

[63] Continuation-in-part of Ser. No. 884,830, Mar. 9, 1978, Pat. No. 4,220,386.

[30] Foreign Application Priority Data

Mar. 10, 1977 [GB] United Kingdom ............ 10280/77

[51] Int. Cl.³ ........................................... H01R 13/52
[52] U.S. Cl. .............................. 339/60 R; 128/419 P; 339/DIG. 3
[58] Field of Search ............... 128/419 P; 339/60, 94, 339/DIG. 3

[56] References Cited

U.S. PATENT DOCUMENTS

| 2,379,942 | 7/1945  | Webber ................... 339/60 C |
| 2,704,355 | 3/1955  | Holton ................... 339/94 A |
| 3,002,126 | 9/1961  | Noir ..................... 339/DIG. 3 |
| 3,344,391 | 9/1967  | Ruete .................... 339/60 R |
| 3,509,296 | 4/1970  | Harshman et al. .......... 339/DIG. 3 |
| 3,871,737 | 3/1975  | Dorrell et al. ............ 339/DIG. 3 |
| 3,880,487 | 4/1975  | Goodman et al. .......... 339/60 R |
| 3,924,639 | 12/1975 | Hess ..................... 339/DIG. 3 |
| 3,936,125 | 2/1976  | Hutter ................... 339/94 C |
| 4,033,355 | 7/1977  | Amundson ................ 128/419 P |
| 4,064,623 | 12/1977 | Moore .................... 339/DIG. 3 |
| 4,072,154 | 2/1978  | Anderson et al. .......... 339/94 C |
| 4,082,405 | 4/1978  | Stepniak ................. 339/DIG. 3 |

*Primary Examiner*—Neil Abrams
*Attorney, Agent, or Firm*—Alexis Barron

[57] ABSTRACT

An electrical socket for use with a spigotted plug and intended primarily for implantation in a human or animal body, for instance to connect an electrode catheter to a cardiac pacemaker casing. The electrical socket has a body defining a bore in which an insulating body portion of a plug member may be received in a sealing manner. A block of conducting rubber is positioned in the bore and has a first recess in which the plug spigot may be received, the cross-section of the spigot being greater than that of the first recess, so that the block is deformed as the spigot enters the recess, to make an electrical connection therewith. A second recess is provided in the block of conducting rubber, spaced from said first recess, to allow accommodation of deformation of the rubber material on a spigot entering the first recess. A contact extends through the wall defining the bore, to connect with the block. The conducting rubber may be a silicone rubber loaded with platinum, titanium or carbon particles.

8 Claims, 6 Drawing Figures

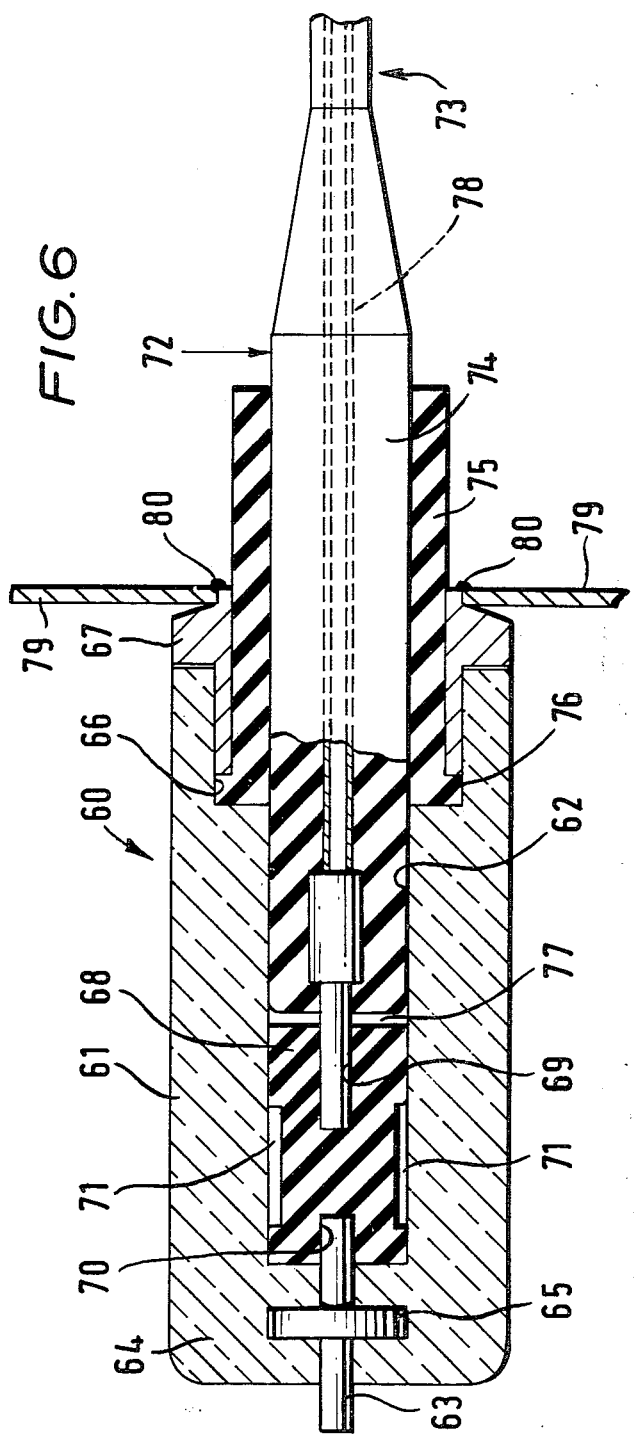

ELECTRICAL SOCKET USEFUL FOR CONNECTING AN ELECTRODE CATHETER TO A CARDIAC PACEMAKER CASING

This Application is a continuation-in-part of earlier application Ser. No. 884830 filed Mar. 9, 1978, now U.S. Pat. No. 4,220,386 in the name of John Kenny, assignor to Needle Industries Limited.

BACKGROUND OF THE INVENTION (a) Field of the Invention

This invention relates to an electrical socket, intended for use with a plug member to form a complete connector suitable for implantation in a human or animal body. The electrical socket of this invention may be used in a cardiac pacemaker system for implantation in a human body, the socket being provided on a pacemaker casing and the plug member on an electrode catheter, to allow electrical connection of the electrode catheter to the pacemaker. Such a pacemaker for implantation is described and claimed in co-pending Application Ser. No. 884966 filed Mar. 9, 1978 and entitled "Cardiac Pacemakers" the entire disclosure of which is incorporated herein by reference. A complete plug and socket connector also is described and claimed in the aforesaid co-pending application Ser. No. 884830.

(b) Description of the Prior Art

With an implanted cardiac pacemaker system, it is most important that the connection between the proximal end of the electrode catheter (the distal end of which communicates with the heart for stimulation thereof) and the implanted cardiac pacemaker (which normally is located some considerable distance from the heart) is very reliable and able to withstand the implanted environment for a considerable number of years. Not only must the connection offer very low electrical resistance, it must furthermore be hermetically sealed against the environment and body fluids at the site of implant. Spring-loaded metal-to-metal connectors together with fluid-tight seals have been used previously, but these have proved in practice to offer an increasing electrical resistance with time, owing to corrosion, and this can in turn lead to premature failure of the overall pacemaker system even though the life of the pacemaker itself has not expired.

OBJECTS OF THE INVENTION

It is a principal object of this invention to provide an electrical socket for use with a corresponding plug, to be suitable for implantation in a body, which socket may make with a plug an electrical connection able to withstand the environment at the site of implantation for long periods of time. A further object is to provide an electrical socket which allows a most reliable connection to be made with a suitable plug member, giving therewith a low contact resistance.

A further object of this invention is to provide an electrical socket which is capable of receiving any of a range of plug members each having a projecting spigot, even though the transverse cross-sectional sizes and shapes of the projecting spigots may vary to a considerable extent.

Yet another object is to provide an electrical socket which is suitable for mounting within a cardiac pacemaker casing, whereby an electrode catheter having suitable plug on the proximal end thereof may be connected to the pacemaker casing.

SUMMARY OF THE INVENTION

In accordance with these and other objects, there is provided an electrical socket for receiving a plug member having an insulating body portion and a conducting spigot projecting from said body portion and for making an electrical connection to the conducting spigot, which electrical socket comprises a body defining a bore for sealingly receiving a plug member body portion, a block of conducting, resilient rubber material located within said bore, the block of rubber material defining a first recess for receiving a plug member spigot and defining a further recess spaced from said first recess for receiving said spigot, and an electrical contact provided through the walls of the socket member defining said bore and making electrical connection with said block of rubber material, and said first recess in said block of conducting rubber material having a smaller cross-sectional dimension than that of said spigot, whereby the block is deformed by insertion of a plug member spigot into said recess to make an electrical connection therebetween, said deformation of the block of rubber material caused by the insertion of said spigot into said first recess being accommodated at least in part by a reduction in volume of said further recess.

In the electrical socket of this invention, the further recess takes up deformation of the block of conducting rubber as the spigot enters the first recess. Provided that the recess is of smaller cross-sectional shape than the smallest spigot to be accommodated, a reliable and low resistance electrical connection can be made to a variety of sizes of spigot, because the conducting rubber is considerably deformable.

BRIEF DESCRIPTION OF THE DRAWINGS

In order that the invention may better be understood it will now be described in greater detail and two specific embodiments thereof given by way of example, reference being made to the accompanying drawings. In the drawings:

FIG. 6 is a cross-sectional view through a second embodiment of electrical socket of this invention, shown with an appropriate plug fitted therein.

DETAILED DESCRIPTION OF THE PREFERRED ARRANGEMENTS

Figure 1:
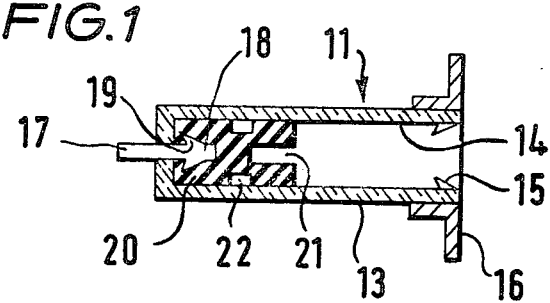
FIG. 1 is a cross-sectional view through a first embodiment of electrical socket arranged in accordance with this invention.

The bore defined by the body of the socket member and which receives the plug member body portion is preferably circular in cross-sectional shape, so as to be able to receive a plug member having a body portion also of circular cross-section and of such dimensions that the body portion is a sealing fit within the bore. By having a body portion which is resiliently deformable and, when relaxed, of a larger overall diameter than the bore of the socket member, the body portion of the plug member when fitted within the bore of the socket member is deformed to effect a fluid and gas tight seal against the wall of the socket member defining the bore. Such a plug member body portion conveniently can be moulded from a natural or silicone rubber, and may be moulded directly on to the conductor.

To assist retention of the plug member within the socket member, the plug member may be provided with one or more projections such as ribs or barbs on its cylindrical body portion, which projections are directed away from the free end of the spigot whereby the plug member may with relative ease be pressed into the bore of the socket member but may be withdrawn therefrom only against the action of the projections. By forming the projections as annular barbs surrounding the body portion of the plug member, the barbs themselves may serve to enhance or form the sealing effect between the wall of the socket member defining the bore and the plug member.

Further to assist the retention of a plug member within the bore of the socket member, an inwardly-projecting annular rib may be provided within the bore, for engagement with the body portion of the plug member.

The conducting rubber material is preferably a silicone rubber which has been loaded with conducting particles such as particles of carbon, titanium or platinum. Silicone rubber loaded with conducting particles is known per se, and exhibits excellent properties when a conductor displaying resilience or flexibility is required; it is thus used for instance when loaded with carbon particles for making contact pads for electrodes which must be maintained in contact with the skin of an animal or human body. The resilient properties in all directions of the loaded rubber material have proved valuable in this invention, in making an excellent electrical connection to the spigot of an inserted plug member.

To ensure the rubber material is deformed on insertion of a spigot in the first recess therefor in the block of conducting rubber material, the first recess should have a smaller cross-sectional dimention than the spigot. For instance, the recess could be of square and the spigot of circular cross-sectional shape, the side of the square being smaller than the diameter of the spigot. Preferably, the first recess is of circular cross-sectional shape and the further recess is of annular channel section extending around the block of conducting rubber material, part-way between the ends thereof. Because the conducting rubber is relatively resilient, a wide range of shapes and sizes of spigot can be accommodated in the first recess, large deformation of the rubber material being taken up by a reduction in volume of the further recess.

The contact making an electrical connection with the block of conducting rubber material preferably is in the form of a metal stud having a barb-like head projecting into the bore and fitting within a correspondingly-shaped, but smaller, recess in the block of conducting rubber material such that the material is deformed to fit thereover. Conveniently, the wall of the socket member defining the bore is made of a ceramic material and the metallic stud—preferably of platinum or titanium—is provided in the wall during manufacture of the socket member so that a hermetic seal is formed therearound. Conveniently, a platinum or titanium flange is provided around the socket member adjacent the end of the bore through which the plug member is inserted, whereby the socket member may be sealed to the body or case of a piece of electrical equipment—for instance a cardiac pacemaker casing. Such sealing may be effected to create a hermetic seal, for example by an electron beam welding technique, and electrolytic corrosion may be avoided in this way. Platinum should be selected for the flange and for the contact when employing a ceramic for the body of the socket member defining the bore, because of the relative ease of forming a hermetic seal between a ceramic material and platinum.

The plug member for use with the socket of this invention may be provided on the end of a conductor which may take a variety of forms, but when the electrical socket is mounted in a pacemaker casing, the plug should be attached to the proximal end of an electrode catheter, the distal end being approximately positioned to stimulate the heart. A suitable plug member may be moulded directly on the proximal end of such a catheter.

Figure 2:
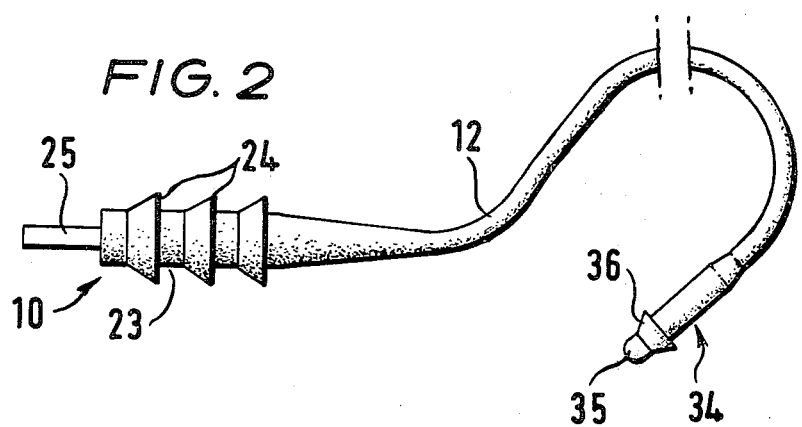
FIG. 2 is a side view of an electrode catheter including a plug member for use with the electrical socket of FIG. 1.
Figure 3:
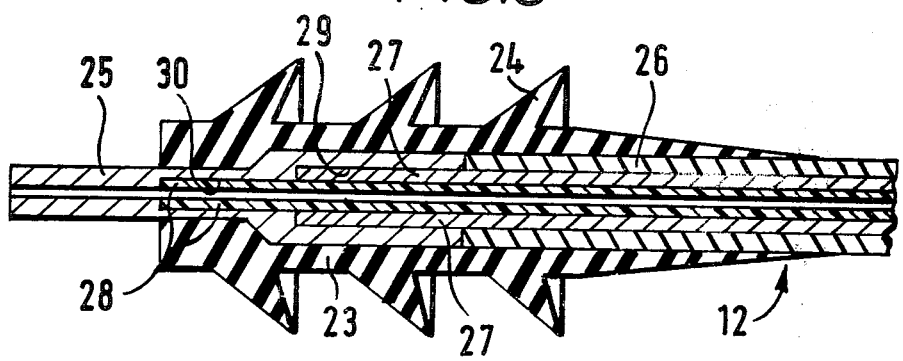
FIG. 3 is a cross-sectional view, but on an enlarged scale, through the plug member shown in FIG. 2, as fitted to an electrode catheter.

Referring initially to FIGS. 1 to 3, there is shown a first embodiment of electrical socket of this invention intended to allow the connection of an electrode catheter having an appropriate plug to a cardiac pacemaker casing carrying the socket. The plug member 10 is adapted to fit into the socket 11, the plug member 10 being moulded directly on the end of the electrode catheter 12 and the socket 11 being adapted for incorporation in the casing of the pacemaker itself.

The socket 11 (FIG. 1) comprises a main body 13 made from a ceramics material and defining a blind circular bore 14. An inwardly directed annular rib 15 is provided within the bore 14, spaced slightly from the open end thereof and upstanding from the wall defining the bore by about 0.1 mm. A circular metallic flange 16 (for instance of platinum or titanium) is provided on the ceramics material body portion 13 around the open end of the bore 14 during the manufacture of the socket member, so that the flange 16 is hermetically bonded to the main body 13. Similarly, a conducting contact 17 is provided through the blind end wall of the main body 13 so as to project into the bore 14. The contact is conveniently of platinum, and is also hermetically sealed to the main body. Within the bore 14, the contact 17 has an enlarged head 18, provided with barbs 19 directed towards the blind end of the bore.

Located within the bore 14 is a block 20 of relatively soft, resilient conducting silicone rubber material, loaded with particles of one of carbon, titanium or platinum to render the block electrically conducting. The block 20 is generally of circular cross-section to fit closely within the bore 14, and has a circular first recess 21 opening co-axially towards the open end of the bore 14. A second co-axial recess is provided for receiving the head 18 of the contact 17, the block 20 being deformed to fit over the head and engage with the barbs 19, thereby making a good electrical connection therebetween. A further recess in the form of an annular channel 22 is provided part-way between the ends of the block 20 of conducting silicone rubber material.

The conducting silicone rubber material is know per se and comprises relatively soft, resilient silicone rubber which has been loaded preferably with titanium particles. Such material displays reasonable electrical conductivity, though the resistance offered depends to some extent upon the degree of compression of the material.

The plug member 10 (FIGS. 2 and 3) comprises a body portion 23 of circular cross-section and is provided with three annular ribs 24, each having the general cross-sectional shape of a barb directed generally away from the free end of the plug member 10. The body portion 23 is moulded from insulating silicone rubber, and is thus flexible, relatively soft and resilient. The material is similar to that of the block 20, except that it has not been loaded with titanium particles; as such the material displays excellent insulating properties. A typical material for this purpose is that known as Dow-Corning MDX-4-4210 Clean-Grade Elastomer. The body portion 23 is moulded around a metal spigot 25, preferably of titanium and which projects from the free end of the body portion for connection with the socket of FIG. 1. The diameter of the spigot 25 should be slightly greater than that of the recess 21 when the block of silicone rubber is located in the bore 14 of the socket 11.

As shown in FIG. 3, the body portion 23 is moulded directly on to an electrode catheter 12, which includes an outer insulating silicone rubber protective sleeve 26, conductors 27 and a plastics core 28. The spigot 25 is shaped to receive in a first counterbore 29 the conductors 27, to make electrical connection therewith, and in a second, smaller counterbore 30 the plastics core 28. The body portion 23 bonds during the moulding operation to the sleeve 26, and if required the spigot 25 can lightly be crimped on the conductors 27 to ensure a reliable electrical connection thereto.

In use, when the plug member 10 is fitted into the socket 11, the spigot 25 enters the first recess 21 in the block 20 of conducting silicone rubber located within the bore 14 and makes therewith an electrical connection of low resistance. By arranging the diameter of the first recess 21 to be of slightly smaller size than that of the spigot 25, the rubber is compressed and resiliently urged into engagement with the spigot, as the spigot enters the first recess 21 and a good electrical connection is thereby achieved. The annular channel 22 allows the rubber to distort and deform as required to allow accommodation of the spigot 25 in the first recess 21. The annular ribs 24, shaped as barbs, allow the body portion 23 of the plug member easily to enter bore 14 of the ceramic body 13 but restrain withdrawal of the plug member owing to their barb-like shape. The rib 24 nearest the catheter 12 rides over and engages behind rib 15 of the socket 11, and further assists in the retention of the plug member within the socket. Moreover, the ribs 24 of the plug member 10 effect a hermetic seal between the body portion 23 of the plug member and the main body 13 of the socket, whereby the electrical connection between the spigot 25 and the block 20 of conducting silicone rubber material is isolated from the surrounding environment. By loading the silicone rubber with titanium and providing a titanium spigot, electrolytic corrosion of the spigot, should seepage of body fluids over a period of years occur, is substantially inhibited.

The electrode catheter 12, which is intended for use in a cardiac pacemaker system and carries the plug member 23, is of a suitable length for such applications and has at its distal end a platinum tip 35 having a rounded free end, there being an axial bore extending into the tip from its other end. In this bore are received the plastics core 28 and the carbon-fibre conductors 27 such that the conductors are connected electrically to the tip 35. The silicone rubber sleeve 26 is moulded directly over part of the tip 35 so as to insulate the greater part thereof and to hold the tip on the core and conductors. A silicone rubber flange 36 is provided at the end of the sleeve 26 so as to assist retention of the electrode in the required position.

Figure 4:
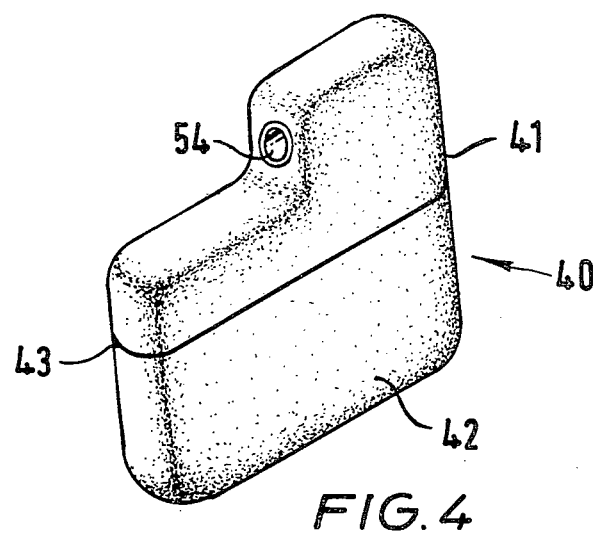
FIG. 4 is a perspective view of a cardiac pacemaker casing incoporating the electrical socket of this invention as shown in FIG. 1.
Figure 5:
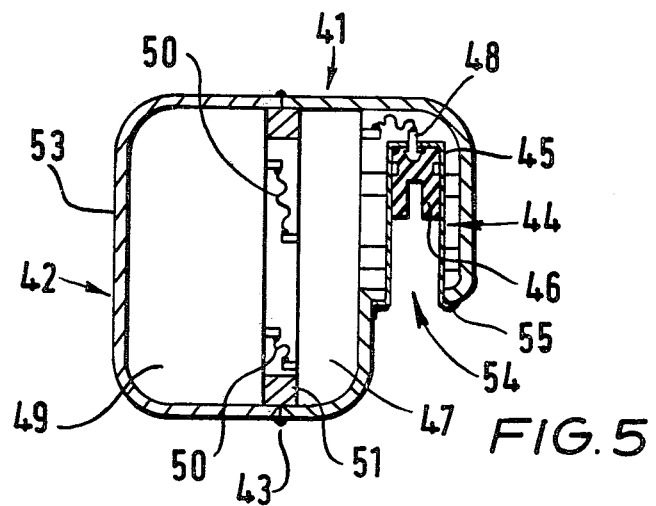
FIG. 5 is a cross-section through the pacemaker casing of FIG. 4.

FIGS. 4 and 5 show a cardiac pacemaker implant case 40, including a socket generally similar to that shown in FIG. 1, and for use with an electrode catheter having a plug member as shown in FIGS. 2 and 3.

The case for the pacemaker comprises two separate moulded plastics chamber parts 41 and 42, which mate together at 43 to define a complete chamber. Part 41 is fitted with a socket member 44, comprising a ceramic body 45 defining a bore in which is located a conducting silicone rubber block 46, connected to an electronic package 47 contained within chamber part 41 by means of contact 48 extending through the ceramic body 45. Within the chamber part 42 is a battery pack 49, connected to the electronic package 47 by means of wires 50. A continuous ring 51 of resilient silicone rubber material is positioned between the electronic package 47 and the battery pack 49 so as to urge the package and pack 47 and 49 respectively apart, into firm engagement with the associated chamber parts 41 and 42. The ring 51 moreover is engaged with the chamber parts 41 and 42 immediately under the mating region 43 of the chamber parts. If required, a layer of silicone rubber can be provided between the inner wall of a chamber part and the package or pack therewithin. The two chamber parts 41 and 42 can be glued together once all the components have been assembled therewithin, by means of an adhesive selected for the plastics material of the chamber parts. For instance, the parts can be of an epoxy resin, and a similar resin used for glueing the parts together.

The entire moulded plastics chamber parts 41 and 42 are covered by a platinum skin 53, also formed in two separate parts which abut in the mating region 43 of the two chamber parts. The skin is shaped from platinum sheet of about 0.25 mm thickness, so as to fit closely over the chamber parts. An aperture 54 is provided in the skin around the opening into the bore of the socket member 44. The abutting edges of two separate parts of the skin 53 are welded together by an electron beam welding technique and the skin is also welded around the aperture 54 to a metal flange 55 around the socket member 44 by the same technique, whereby a continuous, hermetical seal is formed around the entire casing.

The two parts of the platinum skin conveniently are formed by a deep drawing operation from a flat sheet of platinum, using the chamber parts themselves as the male drawing tool. Pure platinum is relatively soft and lends itself to such a forming operation, especially when in a relatively thin sheet, particularly because the material displays virtually no spring-back. However, the skin could be formed separately and then fitted to the assembled chamber parts prior to the welding operation.

An electrical connection must be provided to the platinum skin, to allow a current return from the distal end of a catheter used with the pacemaker case. Conveniently, this is effected by means of the flange 55 of the socket member 44, connected internally back to the electronic package 47 within chamber part 41.

In use, an appropriate electrode catheter fitted with a plug member at its proximal end for insertion into socket member 44 is introduced into the body so that the distal end is within the heart where stimulation is required, and the proximal end is adjacent the site of implanting of the pacemaker case. Next, the plug member 10 of the catheter is inserted into the socket 40 of the pacemaker casing, and the pacemaker is positioned suitably at the implantation site, whereafter the surgery is completed in the usual way.

It is found that the platinum skin, even though serving as a contact for the earth return, is not prone to corrosion or other deterioration, for platinum proves to be virtually inert within the environment of a human or animal body at the usual sites of implantation. Thus the life of the implanted pacemaker will be dictated by the battery pack 49, rather than by the life of the pacemaker casing or the life of the electrode catheter—and battery packs are currently being produced which should call for preventative replacement only every 5 or even 10 years, even though the actual life may be yet longer.

Referring now to FIG. 6, there is shown a second embodiment of electrical socket of this invention, again intended for incorporation in the case of a cardiac pacemaker to receive a plug member fitted on the proximal end of an electrode catheter. The socket 60 comprises a ceramics material body 61 of circular overall cross-sectional shape and defining a blind bore 62 also of circular cross-sectional shape. A pin 63 of titanium or platinum extends through and hermetically is sealed to the end wall 64 of the body, the pin being moulded in position during manufacture of the body 61. The pin 63 includes a flange 65 wholly embedded in the ceramics material body securely to restrain the pin therein. The open end of the body 61 has a counterbore 66, in which is fitted in a sealing manner a titanium collar 67, the collar being so provided during moulding of the ceramics body 61. An annular groove is defined between the inner end of the counterbore 66 and the collar 67.

Located within the bore 62 is a block 68 of resiliently deformable silicone rubber material loaded with titanium particles, to render the material conducting. The block defines a first recess 69 of circular cross-sectional shape and extending axially into the block from the end thereof nearer the open end of the bore, a second recess 70 also of circular cross-sectional shape and extending axially from the other end of the block and in which the inner end of the pin 63 is located, and a further recess 71 in the form of an annular channel extending around the block part-way between the ends thereof. The further recess 71 is of considerable axial extent, having an axial length of approximately half that of the whole block 68. The cross-sectional dimension of the second recess 70 is smaller than that of the inner end of the pin 63, so that an effective low-resistance connection is made thereto.

Fitted within the collar 67 is a silicone rubber sleeve 75, the sleeve having an upstanding flange 76 at the end thereof within the body 61. The flange 76 fits into the annular groove defined between the inner end of the counterbore 66 and the collar 67, and serves both to retain the sleeve within the body 61 and to seal the sleeve to the body.

Also shown in FIG. 6 is a plug member 72 fitted into the socket 60, the plug member being provided on the proximal end of an electrode catheter shown in part at 73. The plug member comprises a body portion 74 of silicone rubber moulded on to the end of the catheter 73, and a spigot 77, projecting from the body portion and connected internally to conductors 78 extending along the catheter within the outer insulating covering thereof. The spigot 77 is made of titanium.

In use, the plug member 72 is inserted into the socket 60 so the spigot 77 enters the first recess 69, with the body portion 74 fitting within the sleeve 75. The body portion 74 of the plug member should be of larger cross-sectional dimensions than the bore of the sleeve 75, when relaxed, so that on inserting the plug member, the sleeve 75 is compressed to effect a tight seal to the plug member body portion. The spigot 77 should be of greater cross-sectional dimensions than the first recess 69 in the block 68, so that an effective, low resistance electrical connection is effected therewith, by deforming the block of conducting rubber material. In view of the shape and size of the channel-shaped further recess 71, a wide range of sizes of spigot can be accommodated in the first recess 69, because extensive deformation of the block 68 may take place, without subjecting the block to great volume changes, volume of the further recess 71 instead being reduced. Moreover, a reliable connection is made between the spigot 77 and the block 68, because by loading the rubber material with titanium and providing a titanium spigot, electrolytic corrosion of the spigot is virtually eliminated, even if body fluids leak into the socket, when implanted in a body.

In addition, a range of sizes of plug member body portions can be accommodated, by virtue of the compressability of the silicone rubber sleeve 75. The sealing effect therebetween can be enhanced by tying a suture around the part of the sleeve 75 projecting beyond the socket body 61, and this has the further advantage of restraining the plug member against withdrawal out of the socket.

The socket is intended for mounting in a pacemaker casing. A part of such a casing is shown at 79, defining an aperture into which the collar 67 is welded, as shown at 80. If required, the sleeve 75 may be provided with a further flange abutting and sealing against the region of the weld 80. Moreover, the sleeve 75 preferably is bonded in position within the collar 67, to assist retention and sealing of the sleeve therewithin.

What is claimed is:

1. An electrical socket for receiving a plug member having an insulating body portion and a conducting spigot projecting from said body portion and for making an electrical connection to the conducting spigot, which electrical socket comprises a body defining a bore for sealingly receiving a plug member body portion, a block of conducting, resilient, rubber material located within said bore, the block of rubber material defining a first recess for receiving the spigot of said plug member and defining a further recess in the form of an annular channel disposed around said block of conducting rubber material, part-way between the ends thereof, and spaced from said first recess and an electrical contact provided through the walls of the socket member defining said bore and making electrical connection with said block of rubber material, and said first recess in said block of conducting rubber material having a smaller cross-sectional dimension than that of said spigot, whereby the block is deformed by insertion of a plug member spigot into said recess to make an electrical connection therebetween, said deformation of the block of rubber material caused by the insertion of said spigot into said first recess being accomodated at least in part by a reduction in volume of said further recess.

2. An electrical socket as claimed in claim 1, in which said conducting rubber material comprises a silicone rubber loaded with conducting particles.

3. An electrical socket as claimed in claim 2, in which the conducting particles loaded in the silicone rubber are selected from particles of carbon, platinum and titanium.

4. An electrical socket as claimed in claim 1, in which said bore defined by the socket member body is of circular cross-sectional shape to receive a correspondingly-shaped plug member body portion.

5. An electrical socket as claimed in claim 1, in which an inwardly-projecting annular rib is provided within said bore, for engagement with the body portion of an inserted plug member.

6. An electrical socket as claimed in claim 1, wherein the cross-sectional shape of said first recess is circular, to receive a plug member spigot of circular but larger cross-sectional shape.

7. An electrical socket as claimed in claim 1, in which said contact making an electrical connection with said block of conducting rubber material is in the form of a metal stud, a barb-like head being provided on said stud and projecting into said bore, said block of conducting rubber material defining a third recess the shape of which corresponds to that of said barb-like head but of a smaller size such that accommodation of said barb-like head in said third recess deforms said rubber material to make an electrical connection with said contact.

8. An electrical socket as claimed in claim 1, in which said socket body comprises walls formed of a ceramic material to define said bore, a platinum stud extending through said walls to connect to said block of conducting rubber material and a metallic mounting flange selected from the group consisting of titanium and platinum bonded to said walls around the opening to said bore.

* * * * *